United States Patent
Gazendam

(10) Patent No.: US 11,274,330 B2
(45) Date of Patent: Mar. 15, 2022

(54) METHOD FOR DETECTING FOOD SPOILAGE MICROBES

(71) Applicant: Original G B.V., Hoogezand (NL)

(72) Inventor: Jurjen Gazendam, Hoogezand (NL)

(73) Assignee: Original G B.V., Hoogezand (NL)

( * ) Notice: Subject to any disclaimer, the term of this patent is extended or adjusted under 35 U.S.C. 154(b) by 162 days.

(21) Appl. No.: 16/619,119

(22) PCT Filed: Jun. 6, 2018

(86) PCT No.: PCT/EP2018/064922
§ 371 (c)(1),
(2) Date: Dec. 4, 2019

(87) PCT Pub. No.: WO2018/224561
PCT Pub. Date: Dec. 13, 2018

(65) Prior Publication Data
US 2020/0115732 A1  Apr. 16, 2020

(30) Foreign Application Priority Data
Jun. 7, 2017  (EP) .................. 17174663.9

(51) Int. Cl.
*C12Q 1/04* (2006.01)
*C07K 7/06* (2006.01)
*C12Q 1/37* (2006.01)
*G01N 21/76* (2006.01)

(52) U.S. Cl.
CPC ............ *C12Q 1/04* (2013.01); *C07K 7/06* (2013.01); *C12Q 1/37* (2013.01); *G01N 21/76* (2013.01)

(58) Field of Classification Search
None
See application file for complete search history.

(56) References Cited

U.S. PATENT DOCUMENTS

| 7,244,583 B2 * | 7/2007 | Sanders | C12Q 1/04 435/23 |
| 7,678,550 B1 * | 3/2010 | Steward | G01N 33/582 435/7.32 |

FOREIGN PATENT DOCUMENTS

| WO | 0210433 | 2/2002 |
| WO | 2016018798 | 2/2016 |
| WO | 2016076707 | 5/2016 |

OTHER PUBLICATIONS

Microbial Food Contamination Edited by Charles L. Wilson, PhD, CRC Press, Chapter 7. Written by Daniel Y.C. Fung pp. 149-186. Oct. 8, 2007.*

Marchand et al.: 'Heterogeneity of heat-resistant proteases from milk *Pseudomonas* species', International Journal of Food Microbiology 133 (2009), 68-77.

* cited by examiner

*Primary Examiner* — Anand U Desai
(74) *Attorney, Agent, or Firm* — N.V. Nederlandsch Octrooibureau; Tamara C. Stegmann; Catherine A. Shultz

(57) ABSTRACT

A method for detecting a food spoilage microbe in a food sample comprising contacting a food sample with a peptide substrate, comprising a fluorescent agent having an emission wavelength of 650-900 nm, a non-fluorescent agent having an absorption wavelength of 650-900 nm, for quenching said emission of said first fluorescent agent, and a cleavage site located between said fluorescent agent and said non-fluorescent agent, b) monitoring the fluorescence of the sample containing the peptide substrate in step a), wherein an increase in fluorescence is indicative for the presence of food spoilage microbes.

16 Claims, 1 Drawing Sheet
Specification includes a Sequence Listing.

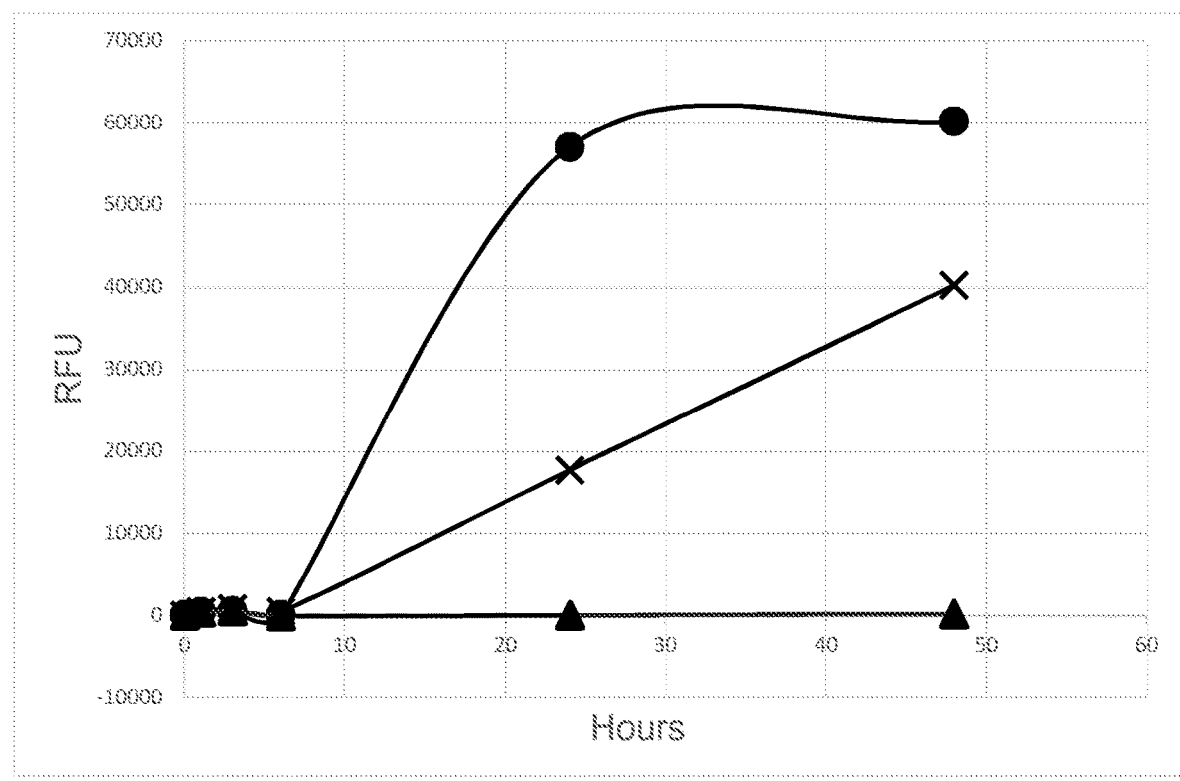

METHOD FOR DETECTING FOOD SPOILAGE MICROBES

FIELD OF THE INVENTION

The present invention relates to a method for detecting food spoilage microbes. The invention also relates to a kit for carrying out the method of the invention.

BACKGROUND ART

Despite best efforts within the food industry, foodstuffs such as dairy products and beverages such as beer and fruit juices can become contaminated with food spoilage microorganisms resulting in shortened shelf lives, less palatable products and in some cases, risks to health.

In the dairy industry, raw milk undergoes different heat and other treatments in order to remove pathogenic microorganisms and to increase the shelf life of milk products. Pasteurization is largely applied to certain food products such as milk in order to decrease the microbiological risk and to increase their preserving ability. Pasteurization is not intended to kill all pathogenic microorganism in food or liquid. UHT (ultra-heat treatment) is also used for milk treatment. UHT processing holds the milk at a temperature of 138° C. for a fraction of second. In countries such as India where milk is produced in a non-standardized way, pasteurization and/or UHT processing is not always effective at inactivating spoilage microorganisms, resulting in milk with a shortened life shelf life. Currently, there is no quick test to determine whether the pasteurization and/or UHT processing has been effective. Samples must be cultured to enable a bacterial count to be conducted in order to determine whether a sample is contaminated or not.

WO2016/018798 relates to in vitro methods for detecting a biomarker of inflammation, infection, and/or bacterial activity in a milk sample from a cow, which indicate issues with the milk itself (i.e., spoilage) or issues related to the health of the cow (i.e., mastitis).

In the brewing industry, there is a need to determine whether a batch has been contaminated with beer spoilage bacteria such as *Lactobacillus lindneri, Lactobacillus brevis* and *Pediococcus damnosus*. PCR has been used to detect beer spoilage microorganisms (S. borg, 2016, 229, Proceedings of World Brewing Congress), however, PCR still requires 24-48 hours to determine the presence of spoilage bacteria. A rapid test is still needed so that minimal delays occur in the production process.

MicroSnap™ *Listeria* spp. (Hygenia) is a test for detection and enumeration of *Listeria* bacteria. The test uses a bioluminogenic test reaction that generates light when enzymes that are characteristic of *E. coli* bacteria react with specialized substrates. The light generating signal is then quantified in the EnSURE™ luminometer. Results are available in 24 hours. However, this method relies on an enrichment of the *Listeria* bacteria. A rapid, on-the-spot test is required to enable fast decision making in a production environment so that food manufacturing processes are not delayed unnecessarily.

It is an object of the present invention to provide a rapid method for the determination of food spoilage microbes.

SUMMARY OF THE INVENTION

The present invention seeks to provide a method for detecting food spoilage microbes in a food sample comprising:

a) adding a first pH adjustment agent to a food sample to provide a food sample having a pH in the range of pH 1 to 5, separating any solid precipitate present in the pH adjusted food sample to provide a pH adjusted food sample and adding a second pH adjustment agent to the pH adjusted food sample to provide a food sample having a pH in the range of pH 6.5-9 to be used in step b), b) contacting a food sample with a peptide substrate, wherein the peptide substrate comprises a peptide comprising a fluorescent agent having an emission wavelength of 650-900 nm, a non-fluorescent agent having an absorption wavelength of 650-900 nm, for quenching said emission of said fluorescent agent, and a cleavage site located between said fluorescent agent and said non-fluorescent agent, the cleavage site cleavable by a protease specifically provided by a food spoilage microbe belonging to a first group consisting of a limited number of microbial strains, species or genera of a food spoilage microbes, and not cleaved by any compound provided by any microbe not belonging to said first group of a food spoilage microbes, c) monitoring the fluorescence of the sample containing the peptide substrate in step b), wherein an increase in fluorescence is indicative for the presence of a food spoilage microbe belonging to said first group of a food spoilage microbes.

According to the present invention, a method as defined above is provided, which enables rapid and specific detection of microorganisms that cause food spoilage. In the presence of a protease that recognises and cleaves the cleavage site, cleaving the peptide at the cleavage site results in release of the first non-fluorescent agent from the peptide substrate, and as a result a fluorescent signal is detectable by a suitable detector. An advantage of the present method is that it can be carried out in raw food samples without the need to enrich the microbe population by, for example, culturing the microbes. As a result, the present method is able to detect bacterial contamination within for example 10 minutes of contacting the peptide substrate with the food sample.

Without wishing to be bound by theory, the inventors postulate that the emission wavelength of the fluorescent agent enables fluorescence to be detected in a region of minimal background fluorescence. Prior art methods rely on monitoring below the 600 nm region by, for example, bioluminergenic or by simple colorimetric detection. Monitoring below the 600 nm region, however, provides insufficient sensitivity due to background emission caused by auto luminescence and/or auto fluorescence of amino acids such as tryptophan, tyrosine and phenylalanine. The method according to the present invention is able to detect the presence of food spoilage microbes in a food sample without the need for enrichment of microbial population.

The invention also provides a kit for the detection of food spoilage microbes comprising:

a) a tube containing a peptide substrate comprising a fluorescent agent having an emission wavelength of 650-900 nm, a non-fluorescent agent having an absorption wavelength of 650-900 nm, for quenching said emission of said fluorescent agent, and a cleavage site located between said fluorescent agent and said non-fluorescent agent, the cleavage site cleavable by a protease specifically provided by a food spoilage microbe belonging to a first group consisting of a limited number of microbial strains, species or genera of a food spoilage microbes, and not cleaved by any compound provided by any microbe not belonging to said first group of a food spoilage microbes, b) a tube comprising a first pH adjustment agent preferably selected from the group consisting of hydrochloric acid, acetic acid, trichloroacetic acid and citric acid, and c) a tube containing a second pH adjustment agent preferably selected from the group consisting of sodium hydroxide, sodium acetate tris buffer and sodium phosphate buffer.

DESCRIPTION OF EMBODIMENTS

The present invention relates to a method for detecting food spoilage microbes comprising:
a) adding a first pH adjustment agent to a food sample to provide a food sample having a pH in the range of pH 1 to 5, separating any solid precipitate present in the pH adjusted food sample to provide a pH adjusted food sample, and adding a second pH adjustment agent to the pH adjusted food sample to provide a food sample having a pH in the range of pH 6.5-9 to be used in step b),
b) contacting a food sample with a peptide substrate, wherein the peptide substrate comprises a peptide comprising a fluorescent agent having an emission wavelength of 650-900 nm, a non-fluorescent agent having an absorption wavelength of 650-900 nm, for quenching said emission of said fluorescent agent, and a cleavage site located between said fluorescent agent and said non-fluorescent agent, the cleavage site cleavable by a protease specifically provided by a food spoilage microbe belonging to a first group consisting of a limited number of microbial strains, species or genera of a food spoilage microbes, and not cleaved by any compound provided by any microbe not belonging to said first group of a food spoilage microbes,
c) monitoring the fluorescence of the sample containing the peptide substrate in step b),
wherein an increase in fluorescence is indicative for the presence of a food spoilage microbe belonging to said first group of a food spoilage microbes.

The term "food spoilage" as used herein means an unsatisfactory change in the sensory characteristics of a foodstuff as a result of contamination by moulds, yeast and bacteria.

The term "food spoilage microbes" as used herein means moulds, yeast or bacteria that cause food spoilage.

The term "food sample" as used herein means a foodstuff or beverage. The foodstuff may be a solid or fluid. Preferably the foodstuff is a fluid, more preferably a liquid.

The term "peptide" as used herein means an oligomer comprising at least 3 amino acids. Preferably, the peptide comprises no more than 20 amino acids. Preferably the peptide comprises between 4 and 20 amino acids, more preferably between 6 and 15 amino acids. The amino acids used may be any amino acid, preferably chosen from the group of naturally occurring amino acids or from the group of synthetic amino acids, in particular derivatives of natural amino acids.

The term "cleavage site" as used herein means an amino acid motif that is cleaved by a specific compound whereby the cleavage site comprises one or more amide bonds. The cleavage site may have the structure XYZ, wherein X is at least one amino acid, Y is a portion of molecular structure composed of at least two amino acids, and Z is at least one amino acid. The amino acids are preferably those that enable binding of the compound which effects cleavage of the first cleavage site.

The term "protease" as used herein means a protein secreted by or present in the membrane of a microbe capable of cleaving an amino acid motif, for example an enzyme, in otherwords a protease or transpeptidase The term "a first group consisting of a limited number of microbial strains, species or genera of food spoilage microbes" as used herein means a class of microbes that share the ability to cleave the cleavage site present in the peptide substrate.

The term 'limited' means that such a group will not comprise all microbes, or all bacteria, but to less i.e. a limited number, so that the release of the non-fluorescent agent is indeed indicative for one or more food spoilage microbes, but not to all or any microbes or bacteria etc.

It has been found that by lowering the pH of a fluid food sample to between pH 1 to 5, proteinaceous material having a isoelectric point in the range of pH 1 to 5 can be easily removed as precipated so that protein that may cause background noise in food sample measurements can be easily removed without effecting the activity of proteases that remain in solution at pH 1 to 5. The resultant solution is then pH adjusted to bring the pH to a pH in the range of pH 6.5 to 9. Preferably, such removal of proteinaceous material is carried out when the food sample is a dairy product, for example yoghurt, cream or milk.

A first pH adjustment agent is added to a fluid food sample to provide a foodstuff sample having a pH in the range of pH 2 to 5, more preferably pH 3 to 5, even more preferably pH 4 to 5. A a second pH adjustment agent is added to the resultant fluid sample to provide a fluid food sample having a pH in the range of pH 7.5-9, more preferably pH 8 to 9.

Separating the solid precipitate from the rest of the sample can be done by, for example, centrifugation, filtering or decanting. Preferably, the solid precipitate is separated by centrifugation.

In a preferred embodiment, the first pH adjustment agent is selected from the group consisting of hydrochloric acid, acetic acid, trichloroacetic acid and citric acid.

In an embodiment, the second pH adjustment agent is selected from the group consisting of sodium hydroxide, sodium acetate, tris buffer and phosphate buffer.

Preferably, the food sample is selected from the group consisting of dairy products, fruit based beverages, soft drinks, beer and wine.

In a preferred embodiment, the dairy product is yoghurt, cheese, butter, curds, cream or milk, preferably milk.

The food sample may have been subjected to a pasteurization or UHT process. Sampling a food sample post pasteurization or UHT process treatment provides an indication as to whether the treatment step has been successful in eliminating food spoilage microorganisms from the sample.

Preferably, the cleavage site is cleaved by a protease provided by bacteria from the genera *Pseudomonas, Bacillus, Clostridium, Corynebacterium, Arthrobacter, Alicylcobacillus, Lactobacillus, Listeria, Microbacterium, Micrococcus*, and *Streptococcus*. Preferably, the bacteria is selected from the group of *Alicyclobacillus, Bacillus*, and *Listeria*. Preferably, the bacteria is selected from the group of *A. acidoterrestris, A acidiphilus, A pomorum, A fastidiosus*.

In some preferred embodiments, the cleavage site is a substrate for a serine protease or serine transpeptidase.

Preferably, the serine protease belongs to the group EC.3.4.21.62, e.g. subtilisin, or the group EC.3.4.24.26 e,g. pseudolysin.

Preferably, the cleavage site has the structure XYZ, wherein X is at least one amino acid, Y is a portion of molecular structure composed of at least two amino acids, and Z is at least one amino acid. X and Z may be any amino acid. Preferably Y comprises a dipeptide consisting of an aliphatic, hydrophobic amino acid and an aromatic or cyclic amino acid or a basic amino acid and a hydrophilic amino acid. The aliphatic hydrophobic amino acid is preferably selected from the group consisting of glycine, alanine, leucine, valine and derivatives thereof. The aromatic or cyclic amino acid is preferably selected from the group consisting of phenylalanine, tyrosine, tryptophan, proline and derivatives thereof. The basic amino acid is preferably lysine and the hydrophilic amino acid is preferably threonine or serine.

Preferably Y comprises a dipeptide that is a combination of alanine-phenylalanine, alanine-tryptophan, alanine-proline or lysine-threonine, more preferably Y is a combination of alanine-phenylalanine, alanine-tryptophan, alanine-proline.

Preferably, the peptide comprises a sequence selected from the group consisting of AAAFALAC (SEQ ID NO: 1), AAFAALAC (SEQ ID NO: 2), AAAAFLAC (SEQ ID NO: 3), FAAAALAC (SEQ ID NO: 4), FAAFALAC (SEQ ID NO: 5).

In a preferred embodiment, the peptide has a sequence selected from the group consisting of AAAFALAC (SEQ ID NO: 1), AAFAALAC (SEQ ID NO: 2), AAAAFLAC (SEQ ID NO: 3), FAAAALAC (SEQ ID NO: 4), FAAFALAC (SEQ ID NO: 5), wherein the peptide substrate is cleaved by protease from the *Pseudomonas, Bacillus, Clostridium, Corynebacterium, Arthrobacter, Microbacterium, Micrococcus,* and *Streptococcus*. In this embodiment, the method according to the invention enable monitoring for contamination by the most prevalent food spoilage organisms. Such monitoring is important in, for example, the dairy industry, when the presence of any food spoilage bacteria in a milk product can decrease shelf life, lead to an unpalatable product or provide a health risk if consumed.

In another preferred embodiment, the cleavage site is cleaved by a protease provided by bacteria from the genera *Bacillus* and wherein the peptide comprises a cleavage site AAAFALAC (SEQ ID NO: 1).

Preferably, the peptide is a substrate for a protease provided by bacteria from the genera *Listeria*, for example *Listeria monocytogenes* and the peptide comprises a sequence selected from the group consisting of AANAKTNC (SEQ ID NO: 6), AANKVTNC (SEQ ID NO: 7), ALNKVTNC (SEQ ID NO: 8), ALNAKTNC (SEQ ID NO: 9). When the peptide has a sequence selected from the group of SEQ ID NO: 6-SEQ ID NO: 9, the peptide contains a cleavage site specific for *Listeria monocytogenes*, so that the peptide substrate is cleaved by a protease provided specifically by *Listeria monocytogenes* but not by a food spoilage microbe belonging to the said species of food spoilage microbes.

In another preferred embodiment, the substrate comprises a second cleavage site that is cleaved by a protease specifically provided by a food spoilage microbe belonging to a second group consisting of a limited number of microbial strains, species or genera, and not cleaved by any compound provided by any microbe not belonging to said second and/or first group.

In another embodiment, the second cleavage site is not the same as the first cleavage site.

Preferably, the fluorescent agent is a cyanine dye having an emission wavelength of 650-900 nm and the non-fluorescent agent is a cyanine dye having an absorption wavelength of 650-900 nm.

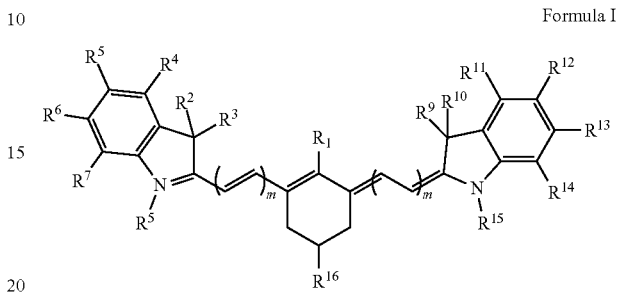

Formula I

In an embodiment, the first fluorescent agent is a cyanine dye having the general formula as shown in formula I, wherein $R^1$ is selected from the group consisting of H, halo, and $$X-\phantom{}\underset{}{\underset{}{\bigcirc}}-R^{17},$$

where $R^{17}$ is selected from the group consisting of carboxyl, amino and sulfanato; X is selected from the group consisting of O, S, NH and N-hydrocarbyl; $R^2$, $R^3$, $R^9$, $R^{10}$ are each independently selected from the group consisting of H and hydrocarbyl; $R^4$, $R^5$, $R^{11}$, $R^{12}$ are each independently selected from the group consisting of H, hydrocarbyl and sulfanato or together with the atoms to which they are bonded form an aromatic ring; $R^6$, $R^7$, $R^{13}$, $R^{14}$ are each independently selected from the group consisting of H and hydrocarbyl, $R^8$ and $R^{15}$ are each independently selected from the group consisting of hydrocarbyl, $(CH_2)qFG$ or $(CH^2)_pLN$ wherein at least one of $R^8$ and $R^{15}$ is $(CH_2)qFG$, wherein q is an integer from 1 to 20 and FG is a functional group that does not directly react with carboxyl, hydroxyl, amino or thiol groups, wherein p is an integer from 1 to 20 and LN is a linker group that reacts with carboxyl, hydroxyl, amino or thiol groups; $R^{16}$ is H or hydrocarbyl.

Preferably, the fluorescent agent is an agent wherein $R^1$ is $$X-\phantom{}\underset{}{\underset{}{\bigcirc}}-R^{17}$$

wherein X is O and $R^{17}$ is $SO_3Na$; $R^2$, $R^3$, $R^9$, $R^{10}$ are hydrocarbyl, preferably methyl; $R^4$ and $R^{11}$ are H and $R^5$ and $R^{12}$ are H or sulfanato; $R^6$, $R^7$, $R^{13}$, $R^{14}$ are H; R8 is $(CH_2)qFG$ where q is 4 and FG is sulfanato; $R^{15}$ is $(CH_2)_pLN$ where p is 5 and LN is carboxyl, $R^{16}$ is H.

Even more preferably, the fluorescent agent is an agent wherein $R^1$ is

wherein X is O and $R^{17}$ is $SO_3Na$; $R^2$, $R^3$, $R^9$, $R^{10}$ are methyl; $R^4$ and $R^{11}$ are H and $R^5$ and $R^{12}$ are sulfanato; $R^6$, $R^7$, $R^{13}$, $R^{14}$ are H; R8 is $(CH_2)qFG$ where q is 4 and FG is sulfanato; $R^{15}$ is $(CH_2)_pLN$ where p is 5 and LN is carboxyl, $R^{16}$ is H. Preferably, the fluorescent agent is an agent corresponding to formula II.

Formula II

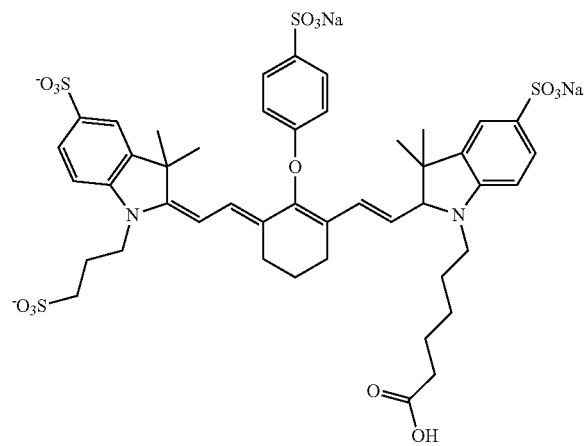

The non-fluorescent agent having an absorption wavelength of 650-900 nm, is a compound that has little or no intrinsic fluorescence and which can efficiently quench the fluorescence from a proximate fluorophore with little background. In an embodiment the non-fluorescent agent is a cyanine molecule. Cyanine molecules, also referred to as cyanine dyes, include compounds having two substituted or unsubstituted nitrogen-containing heterocyclic rings joined by a polymethine chain.

In a preferred embodiment, the non-fluorescent agent is an agent wherein $R^1$ is chloro, $R^2$, $R^3$, $R^9$, $R^{10}$ are methyl; $R^4$ is H and $R^5$ is N-hydrocarbyl, preferably $N[(CH_2)_3SO_3Na]_2$; $R^{11}$ and $R^{12}$ form a aromatic ring monosubstituted with sulfanato group; $R^6$, $R^7$, $R^{13}$, $R^{14}$ are H; $R^8$ is $(CH_2)qFG$ where q is 3 and FG is sulfanato; $R^{15}$ is $(CH_2)_pLN$ where p is 5 and LN is carboxyl; $R^{16}$ is H.

In another embodiment, the fluorescent agent and the non-fluorescent are the same agent, preferably wherein $R^1$ is

in X is O and $R^{17}$ is $SO_3Na$, $R^2$, $R^3$, $R^9$, $R^{10}$ are hydrocarbyl, preferably methyl, $R^4$, $R^5$, $R^{11}$, $R^{12}$, are H, $R^6$, $R^7$, $R^{13}$, $R^{14}$ are H, $R^8$ is $(CH_2)qFG$ where q is 4 and FG is sulfanato, $R^{15}$ is $(CH_2)PLN$ where p is 5 and LN is carboxyl, $R^{16}$ is H.

The non-fluorescent agent may also be a quenching moiety for example BHQ3, (Biosearch) QC-1 (Li-COR-.com), or particles comprising such compounds, for example gold nanoparticles and ferro-nanoparticles. In an embodiment, the peptide substrate is a nanoparticle comprising a peptide as defined herein.

Examples of fluorescent agents that can be used with in present invention include, but are not limited to, Alexa Fluor® 660, Alexa Fluor® 680, Alexa Fluor® 700, Alexa Fluor® 750 ATTO 680, ATTO 700, DY-647, DY-650, DY-673, DY-675, DY-676, DY-680, DY-681, DY-682, DY-690, DY-700, DY-701, DY-730, DY-731, DY-732, DY-734, DY-750, DY-751, DY-752, DY-776, DY-781, DY-782, DY-831, La Jolla Blue, Cy5, Cy5.5, Cy7, IRDye® 800CW, IRDye® 38, IRDye® 800RS, IRDye® 700DX, IRDye® 680, among others. "Alexa Fluor" dyes are available from Molecular Peptides Inc., Eugene, Oreg., U.S.A. (www.peptides.com). "ATTO" dyes are available from ATTO-tec GmbH, Siegen, Germany (www.atto-tec.com). "DY" dyes are available from Dyomics GmbH, Jena, Germany (www.dyomics.com). La Jolla Blue is available from Hyperion Inc. "Cy" dyes are available from Amersham Biosciences, Piscataway, N.J., U.S.A. (www.amersham.com). "IRDye® infrared dyes" are available from LI-COR® Bioscience, Inc. Lincoln, Nebr., U.S. A (www.li-cor.com).

Preferably, the method does not comprise a step of enriching the microbe population. Advantageously, the present invention can detect the presence of food spoilage microorganisms without needing to first enrich the number of microorganisms present by culturing the sample for a number of hours.

In an embodiment, the method comprises contacting the sample with a peptide substrate comprising a second peptide comprising a second cleavage site that is cleaved by a protease specifically provided by a food spoilage microbe belonging to a second group consisting of a limited number of microbial strains, species or genera, and not cleaved by any compound provided by any microbe not belonging to said second or first group.

In another aspect, the present invention relates to a kit for the detection of food spoilage microbes comprising:
a) a tube containing a peptide substrate comprising a fluorescent agent having an emission wavelength of 650 900 nm, a non-fluorescent agent having an absorption wavelength of 650-900 nm, for quenching said emission of said fluorescent agent, and a cleavage site located between said fluorescent agent and said non-fluorescent agent, the cleavage site cleavable by a protease specifically provided by a food spoilage microbe belonging to a first group consisting of a limited number of microbial strains, species or genera of a food spoilage microbes, and not cleaved by any compound provided by any microbe not belonging to said first group of a food spoilage microbes,
b) a tube comprising a first pH adjustment agent preferably selected from the group consisting of hydrochloric acid, acetic acid, trichloroacetic acid and citric acid,
c) a tube comprising a second pH adjustment agent preferably selected from the group consisting of sodium hydroxide, sodium acetate, tris buffer and phosphate buffer.

In a preferred embodiment, the kit comprises a device for monitoring fluorescence, wherein said device is adapted to receive a tube containing a food sample and the peptide substrate.

The embodiments describes for the method apply mutatis mutandis to the kit according to the present invention.

Advantageously, the kit enables a food spoilage microbes to be detected in a simple way without the need for first culturing the sample. The kit can be used in a production environment and does not require specialist laboratory equipment.

The present invention has been described above with reference to a number of exemplary embodiments as shown in the drawing. Modifications and alternative implementations of some parts or elements are possible, and are included in the scope of protection as defined in the appended claims.

BRIEF DESCRIPTION OF THE DRAWING

FIG. 1 shows a plot of RFU vs time for milk samples contaminated with *Pseudomonas aeruginosa* (circle), *Bacillus Cereus* (cross) and *Ochrobactrum anthropic* (triangle).

EXAMPLES

Example 1

Peptide 1 QC-1-AAAFALAC-IRDye800CW was obtained by standard solid phase peptide synthesis methods. Fluorescent agent IRDye800CW and non-fluorescent agent (quencher) QC-1 were obtained from LI-COR (Nebraska, USA).

Alcalase, Sigma Aldrich P4860—stock contains 150 mg/mL alcalase.

Fluorescence was monitored over time using a Cary Eclipse Instrument, settings: Ex. Wavelength: 720 nm; Em. Wavelength: 785 nm; Ex. Slit 10 nm; Em. Slit 10 nm; Ave. Time 0.1 s; Ex. Filter and Em. Filter: Auto General Method 100 µL of a milk or blank (sodium phosphate buffer, pH 8) was diluted into 1.5 mL milliQ water. 100 µL of the diluted sample was added to 1 mL, 0.1M sodium phosphate buffer pH 8, 1.9 mL MQ water, 30 µL peptide 1.10, 2.5 or 0.5 ng/µL of a 123.8 ng/µl solution of Alcalase, a protease secreted by *Bacillus licheniformis*, a microorganism found in raw milk.

Optionally, the milk was pH adjusted to remove acid insoluble proteins. 1 mL of milk was pH adjusted to pH 4.6 by 0.1 mL 10% acetic acid. Solutions were kept at room temperature for 15 minutes, 0.1 mL 1M sodium acetate buffer was added and the samples were centrifuged for 30 minutes at 4500 g. 100 µL of the supernatant was used for sample testing.

TABLE 1 general method

| Run | MilliQ water (ml) | 0.1M Phos. Buffer pH 8 (ml) | Diluted sample (µL) | 1.0 mg/ml peptide (µL) | Alcalase solution 124 ng/mL (µL) | Conc Alcalase ng/mL |
|---|---|---|---|---|---|---|
| 1 | 1.9 | 1 | 100 | 30 | 10 | 1.24 |
| 2 | 1.9 | 1 | 100 | 30 | 2.5 | 0.3 |
| 3 | 1.9 | 1 | 100 | 30 | 0.5 | 0.006 |
| 4 | 1.9 | 1 | 100 | 30 | 0 | 0 |
| 5 | 1.9 | 1 | 100 | 0 | 10 | 1.24 |

TABLE 2

Results

| Sample | Limit of detection at 10 minutes incubation (ng/mL) |
|---|---|
| Milk (not pH treated) | 1.24 |
| Milk (pH treated) | 0.006 |

The results show that the present invention is able to detect the present of bacterial protease directly in a food sample. A sample preparation step can increase the level of detection in milk by a factor of ca. 200.

Example 2

A experiment was conducted to assess the selectivity of the present invention for food spoilage microbes.

Bacterial cultures (*Pseudomonas aeruginosa, Bacillus Cereus, Ochrobactrum anthropic*) were grown overnight at 35° C. on blood agar plates and identification was confirmed using Maldi-TOF (MALDI Biotyper 2.0, Bruker Daltonics, model: Microflex LT, software version 4.1.60)

From the grown colonies, 0.5 McFarland suspensions were prepared in phosphate buffered saline (pH 7.4). 0.5 mL of these suspensions were used to spike 5 mL UHT milk that had been pH adjusted as described above. UHT milk spiked with 75 ng/ml alcalase was used as positive control. A milk sample without alcalase and not spiked with bacterial suspensions was used as negative control.

All milk samples were incubated at 35° C., until measurements were taken using a hand held fluorimeter (DeNiro NIR Flurometer, DetactDiagnostics BV, The Netherlands), at 0, 1, 3, 6, 24 and 48 hours. The RFU for the control sample (phosphate buffered saline) was subtracted from each measurement.

The results shown in FIG. 1 show that fluorescence was detected in milk samples contaminated with *Pseudomonas aeruginosa* (circle), *Bacillus Cereus* (cross) within 10 hours whereas even after 48 hours no fluorescence could be detected in the *Ochrobactrum anthropi* (triangle) sample, thus showing the method of the present invention is selective for food spoilage bacteria over environmental bacteria such as *Ochrobactrum anthropi*.

The invention claimed is:

1. A method for detecting a food spoilage microbe in a food sample comprising:
   a) adding a first pH adjustment agent to a food sample to provide a food sample having a pH in the range of pH 1 to 5, separating any solid precipitate present in the pH adjusted food sample to provide a pH adjusted food sample,
   adding a second pH adjustment agent to the pH adjusted food sample to provide a food sample having a pH in the range of pH 6.5-9 to be used in step b)
   b) contacting a food sample with a peptide substrate, wherein the peptide substrate comprises a peptide comprising a fluorescent agent having an emission wavelength of 650-900 nm, a non-fluorescent agent having an absorption wavelength of 650-900 nm, for quenching said emission of said fluorescent agent, and a cleavage site located between said fluorescent agent and first non-fluorescent agent, the cleavage site cleavable by a protease specifically provided by a food spoilage microbe belonging to a first group consisting of a limited number of microbial strains, species or genera, and not cleaved by any compound provided by any microbe not belonging to said first group of food spoilage microbes,
   c) monitoring the fluorescence of the sample containing the peptide substrate in step b),
   wherein an increase in fluorescence is indicative for the presence of a food spoilage microbe belonging to said first group
   and wherein the peptide comprises a cleavage site selected from the group consisting of AAAFALAC (SEQ ID NO: 1), AAFAALAC (SEQ ID NO: 2), AAAAFLAC (SEQ ID NO: 3), FAAAALAC (SEQ ID NO: 4), FAAFALAC (SEQ ID NO: 5).

2. The method according to claim 1, wherein the first pH adjustment agent is selected from the group consisting of hydrochloric acid, acetic acid, trichloroacetic acid and citric acid.

3. The method according to claim 1, wherein the second pH adjustment agent is selected from the group consisting of sodium hydroxide, sodium acetate, tris buffer and phosphate buffer.

4. The method according to claim 1, wherein the food sample is selected from the group consisting of dairy products, fruit based beverages, soft drinks, beer and wine.

5. The method according to claim 4, wherein the dairy product is yoghurt, cheese, butter, curds, cream or milk.

6. The method according to claim 1, wherein the cleavage site is cleaved by a protease provided by bacteria from the genera *Pseudomonas, Alicyclobacillus, Bacillus, Clostridium, Corynebacterium, Arthrobacter, Lactobacillus, Listeria, Microbacterium, Micrococcus*, and *Streptococcus*.

7. The method according to claim 1, wherein the cleavage site is cleaved by a protease provided by bacteria from the genera *Bacillus* and wherein the peptide comprises a cleavage site AAAFALAC (SEQ ID NO: 1).

8. The method according to claim 1, wherein the cleavage site is cleaved by a protease provided by *Listeria monocytogenes* and the peptide comprises a cleavage site selected from the group consisting of AANAKTNC (SEQ ID NO: 6), AANKVTNC (SEQ ID NO: 7), ALNKVTNC (SEQ ID NO: 8), ALNAKTNC (SEQ ID NO: 9).

9. The method according to claim 1, wherein said fluorescent agent is a cyanine dye having an emission wavelength of 650-900 nm and wherein the non-fluorescent agent is a cyanine dye having an absorption wavelength of 650-900 nm.

10. The method according to claim 1, wherein the method does not comprise a step of enriching the microbe population.

11. A kit for the detection of food spoilage microorganisms comprising:
   a) a tube containing a peptide substrate comprising a fluorescent agent having an emission wavelength of 650 900 nm, a non-fluorescent agent having an absorption wavelength of 650-900 nm, for quenching said emission of said fluorescent agent, and a cleavage site located between said fluorescent agent and said non-fluorescent agent, the cleavage site cleavable by a protease specifically provided by a food spoilage microbe belonging to a first group consisting of a limited number of microbial strains, species or genera of a food spoilage microbes, and not cleaved by any compound provided by any microbe not belonging to said first group of a food spoilage microbes, and wherein the peptide comprises a cleavage site selected from the group consisting of AAAFALAC (SEO ID NO: 1), AAFAALAC (SEQ ID NO: 2), AAAAFLAC (SEQ ID NO: 3), FAAAALAC (SEQ ID NO: 4), FAAFALAC (SEQ ID NO: 5)

b) a tube comprising the a first pH adjustment agent, c) a tube comprising a second pH adjustment agent.

12. The kit according to claim 11, comprising a device for monitoring fluorescence, wherein said device is adapted to receive a tube containing a food sample and the peptide substrate.

13. The kit according to claim 11, wherein the peptide comprises a cleavage site selected from the group consisting of AANAKTNC (SEQ ID NO: 6), AANKVTNC (SEQ ID NO: 7), ALNKVTNC (SEQ ID NO: 8), and ALNAKTNC (SEQ ID NO: 9).

14. The kit according to claim 11, wherein said fluorescent agent is a cyanine dye having an emission wavelength of 650-900 nm and wherein the non-fluorescent agent is a cyanine dye having an absorption wavelength of 650-900 nm.

15. The kit according to claim 11, wherein the first pH adjustment agent is selected from the group consisting of hydrochloric acid, acetic acid, trichloroacetic acid and citric acid.

16. The kit according to claim 11, wherein the second pH adjustment agent is selected from the group consisting of sodium hydroxide, sodium acetate, tris buffer and phosphate buffer.

* * * * *

SEQUENCE LISTING

<160> NUMBER OF SEQ ID NOS: 9

<210> SEQ ID NO 1
<211> LENGTH: 8
<212> TYPE: PRT
<213> ORGANISM: Artificial Sequence
<220> FEATURE:

```
<223> OTHER INFORMATION: Synthetic peptide

<400> SEQUENCE: 1

Ala Ala Ala Phe Ala Leu Ala Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Ala Ala Phe Ala Ala Leu Ala Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Ala Ala Ala Ala Phe Ala Leu Ala Cys
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Phe Ala Ala Ala Ala Leu Ala Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Phe Ala Ala Phe Ala Leu Ala Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Ala Ala Asn Ala Lys Thr Asn Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 7

Ala Ala Asn Lys Val Thr Asn Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Ala Leu Asn Lys Val Thr Asn Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Ala Leu Asn Ala Lys Thr Asn Cys
1               5
```